United States Patent [19]

Savarese et al.

[11] 4,192,877
[45] Mar. 11, 1980

[54] NEUROMUSCULAR BLOCKING AGENTS

[75] Inventors: John J. Savarese, Boxford; Richard J. Kitz, Dover, both of Mass.; Sara Ginsburg, New York, N.Y.

[73] Assignee: Massachusetts General Hospital, Boston, Mass.

[21] Appl. No.: 921,713

[22] Filed: Jul. 3, 1978

Related U.S. Application Data

[63] Continuation-in-part of Ser. No. 820,794, Aug. 1, 1977, abandoned.

[51] Int. Cl.² .................. A61K 31/47; C07D 217/10; C07D 217/20
[52] U.S. Cl. .................................. 424/258; 546/140; 546/149
[58] Field of Search ...... 260/288 CE, 286 Q, 283 BZ; 424/258; 546/140

[56] References Cited

U.S. PATENT DOCUMENTS 3,004,031  10/1961   Taylor et al. .................. 260/286

OTHER PUBLICATIONS

Gladych, et al., Chemical Abstracts, vol. 57, 3411i--3413f (1962).
Kitz, et al., Biochemical Pharmacology, vol. 18, pp. 871-881 (1969).
Danilov, et al., Br. J. Pharmac., vol. 44, pp. 765-778 (1972).
Savarese, et al., Acta Anaesth. Scand. Suppl., 53, pp. 43-58 (1973).
Savarese, et al., Anesthesia & Analgesia, Current Researches, vol. 52, No. 6, pp. 982-988 (1973).
Savarese, et al., Anesthesia & Analgesia, Current Researches, vol. 54, No. 5, pp. 669-678 (1957).
Brittain, et al., Brit. J. Pharmacol., vol. 17, pp. 116-123 (1961).

Primary Examiner—Glennon H. Hollrah
Assistant Examiner—Diana G. Rivers

Attorney, Agent, or Firm—Donald Brown

[57] ABSTRACT

Short acting reversible neuromuscular blocking agents of the formula (I)

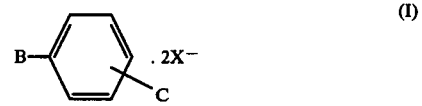

where B and C is preferably meta or maybe para

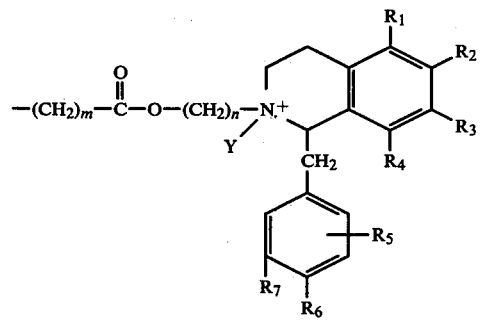

where
m is 2, 3 or 4 and is preferably 2,
$R_1$, $R_2$, $R_3$, $R_4$, $R_5$, $R_6$ and $R_7$ are the same or different and are hydrogen or lower alkoxy of 1 to 4 carbon atoms
Y is lower alkyl of 1 to 4 carbon atoms
n is 2, 3 or 4, most preferably 3, provided that at least one of $R_1$ to $R_4$ and one of $R_5$ to $R_7$ is lower alkoxy and X is a pharmaceutically acceptable anion. These neuromuscular blocking agents of formula I are useful upon administration to a patient in providing muscular relaxation in the patient during surgery and are normally intravenously administered in a pharmaceutically acceptable carrier.

54 Claims, No Drawings

NEUROMUSCULAR BLOCKING AGENTS

This application is a continuation-in-part of now abandoned U.S. patent application Ser. No. 820,794 filed Aug. 1, 1977.

BACKGROUND OF THE DISCLOSURE

In anesthesia, neuromuscular blocking agents are used to provide skeletal muscular relaxation during surgery and during intubation of the trachea.

In general there are two types of neuromuscular blocking agents in use, nondepolarizing and depolarizing.

The nondepolarizing agents include d-tubocurarine, pancuronuim gallamine, diallyltoxiferine, and toxiferine.

The depolarizing agents include succinylcholine and decamethonium. All of the conventional nondepolarizing agents when used for producing skeletal muscle relaxation in surgery have a long duration of action e.g., 60 to 180 minutes in man.

The depolarizing agents on the other hand provide muscle relaxation at dosages normally used for surgery which is less than the duration of action of nondepolarizing agents.

For example, succinylcholine provides a short duration of action of about 5 to 15 minutes whereas decamethonium provides about 20 to 40 minutes duration of muscle relaxation.

To the best of applicants' knowledge, there are no nondepolarizing agents currently available for approved clinical use which have a short duration of action.

As used herein a short duration of action is defined as less than about 10 minutes in the monkey.

The long duration of action of nondepolarizing agents is unacceptable in many surgical procedures which take less than one hour because the patient is not generally fully recovered from their effects e.g., the patient may be unable to breathe adequately on his or her own.

Each nondepolarizing agent has inherent side-effects. For example, gallamine and pancuronium may cause tachycardia, and d-tubocurarine and diallyltoxiferine may cause hypotension.

While such drugs can be pharmacologically antagonized with anticholinesterase agents, this obviously necessitates the administration of a second drug which itself may have its own side effects e.g., bradycardia, gut spasm and bronchorrhea. Thus, to overcome the aforementioned side effects of the anticholinesterase agents, a third drug, an anticholinergic drug e.g., atropine must also be given.

The depolarizing agents to the best of applicants' knowledge have no pharmacologic antagonists. While in most cases there is no need to reverse the effects of the depolarizing agents, in certain patients the effects of succinylcholine are much prolonged because of abnormal metabolism of the agent by the patient.

The depolarizing agents due to that mode of action which initially causes skeletal muscle contraction and stimulation of smooth muscles are also known to cause the following side effects in certain instances: increased intraocular, and intragastric tension, cardiac arrhythmias, potassium release, and muscle pain.

These side effects caused by the depolarizing agents are not caused by the nondepolarizing agents. It is therefore clearly evident that a new neuromuscular blocking agent is needed which would combine the short duration of action of the depolarizing agents with the relatively few side effects and the reversibility of the nondepolarizing agents.

It should be understood that while nondepolarizing agents generally have few side effects, gallamine and pancuronium may cause tachycardia and d-tubocurarine and diallyltoxiferine may cause hypotension.

Surprisingly, the compounds of the present invention also appear to be free of these side effects at the dosages anticipated being used clinically in tests made to date. Reference may be had to the text of:

"The Pharmacological Basis of Therapeutics"—Fifth Edition, edited by Louis S. Goodman and Alfred Gilman published by The McMillian Co., copyright 1975, Chapter 28, author George B. Koelle, for further description of neuromuscular blocking agents.

Reference should also be had to the following articles:

"Neuromuscular Blocking Activity of a New Series of Quaternary N-Substituted Choline Esters"—British Journal of Pharmacology, Sept., 1971, vol. 43, No. 1, p. 107;

"The Pharmacology of New Short Acting Nondepolarizing Ester Neuromuscular Blocking Agents: Clinical Implications"—published in Anesthesia and Analgesia . . . Current Researches, Vol. 52, No. 6, p. 982, Nov.-Dec., 1973;

"Potential Clinical Uses of Short-Acting Nondepolarizing Neuromuscular-Blocking Agents as Predicted from Animal Experiments"—published in Anesthesia and Analgesia . . . Current Researches, Vol 54, No. 5, p 669, Sept.—Oct., 1974; and U.S. Pat. No. 3,491,099, for a further description of neuromuscular blocking agents.

BRIEF DESCRIPTION OF THE DISCLOSURE

The present invention provides new and improved neuromuscular blocking agents sometimes called muscle relaxants which combine a nondepolarizing mode of action with the short duration of action and reversibility needed to meet ideal clinical requirements for use during surgery.

The neuromuscular blocking agents of this invention are represented by the formula (I)

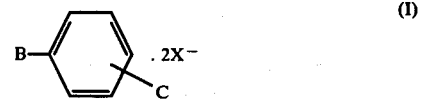

where C is most preferably meta to B as in formula (II)

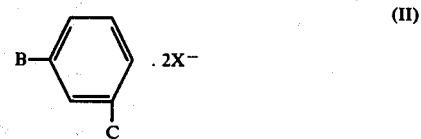

or C is para to B as in formula III

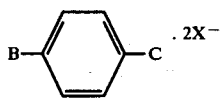

(III)

and where B and C are

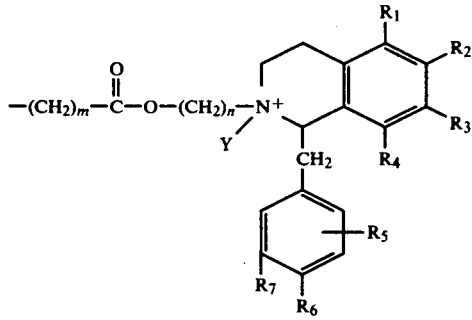

where
- m is 2, 3 or 4 and is preferably 2,
- $R_1$, $R_2$, $R_3$, $R_4$, $R_5$, $R_6$ and $R_7$ are the same or different and are hydrogen or alkoxy of 1 to 4 carbon atoms, (methoxy, ethoxy, propoxy or butoxy).
- Y is alkyl of 1 to 4 carbon atoms (methyl, ethyl, propyl or butyl),
- n is 2, 3 or 4 most preferably 3 and X is a pharmaceutically acceptable anion, provided that at least one of $R_1$ to $R_4$ is always lower alkoxy and at least one of $R_5$ to $R_7$ is always lower alkoxy. The preferred compounds of this invention are those in which $R_5$ to $R_7$ are each lower alkoxy.

Of the compounds of the invention, the most preferred are the compounds of formula II or III where Y is methyl, m is 2, n is 3, $R_5$, $R_6$ and $R_7$ are methoxy at the 3, 4 and 5 positions of the phenyl portion of the benzyl group, $R_1$ and $R_4$ are hydrogen and $R_2$ and $R_3$ are methoxy since these compounds appear to be less quickly hydrolyzed than the dimethoxy benzyl compounds and the meta compound (formula II) is even more preferred than the corresponding para compound because it is significantly shorter acting. The most preferred compounds also exhibit minimal side effects and high potency.

Of the anions of the invention, the following are examples of those which are suitable: iodide, mesylate, tosylate, bromide, chloride, sulfate, phosphate, hydrogen phosphate, acetate, benzene sulfonate, nitrobenzene sulfone, naphthylene sulfonate, and propionate. The mesylate and chloride cations are most preferred because of the solubility of the salt made therefrom in water. Since the activity is in the cation portion of the compound, the nature of the anion is unimportant as long as it is pharmaceutically acceptable.

The compounds of formula I, II or III are used as neuromuscular blocking agents in conjunction with surgery or for intubation of the trachea by conventional parenteral administration e.g., intramuscular or intravenous administration in solution. The compounds of the present invention shown in formulas I, II or III are administered to patients such as monkeys and man (humans) and other mammals to achieve a neuromuscular block. The dosage for each type of patient will vary because of the peculiarities of the species, however, a suitable intravenous amount or dosage of the compounds of formula I, II or III for monkey would be 1.0 to 4.0 mg/kg of body weight, and for a man 0.2 to 3.0 mg/kg of body weight, and most preferably 0.5 to 1.5 mg/kg of body weight, the above being based on the weight of the cation which is the active ingredient.

The dosage for intramuscular administration is two to four times the intravenous dose. The compounds of this invention would normally be readministered every 5 to 20 minutes preferably 5 to 15 minutes after initial administration or given as a continuous infusion depending upon the length of time a muscular block is desired, and as determined by the anesthetists and surgeon in charge of the patient. The compounds of this invention are reverible using conventional anticholinesterase agents such as neostigmine and edrophonium and appear to avoid the side effects associated with the depolarizing agents.

The compounds of formula I, II or III are therefore useful for producing a short duration neuromuscular blockade, and the present invention provides a method of producing such blockade in mammals e.g., man, or monkeys, by intravenously injecting a dose of 0.05 to 4.0 mg/kg to the mammal.

The compounds may be presented in a pharmaceutical formulation for parenteral administration. The formulation may be an aqueous or non-aqueous solution or emulsion in a pharmaceutically acceptable liquid or mixture of liquids, which may contain bacteriostatic agents, antioxidants, buffers, thickening agents, suspending agents or other pharmaceutically acceptable additives. Such formulations are normally presented in unit dosage forms such as ampoules or disposable injection devices, or in multidose forms such as a bottle from which the appropriate dose may be withdrawn. All such formulations should be rendered sterile.

The compounds of this invention may be presented as a powder e.g., as a unit dose in a sealed vial to which sterile water or other pharmaceutically acceptable sterile liquid vehicle may be added by a needle.

A suitable unit dose to obtain a neuromuscular block for mammals e.g., humans or monkeys is about 10 mg to 400 mg and most preferably 50 to 300 mg.

The compounds of this invention if desired may be administered in conjunction with other non-depolarizing agents such as listed above.

Thus a suitable pharmaceutical parenteral preparation will preferably contain 10 to 400 mg of the compounds of formulas I, II or III of this invention in solution.

A simple and preferred formulation is a solution of the compound of formula I, II or III in water which may be prepared by simply dissolving the compound into previously sterilized pure water i.e., pyrogon free water under aseptic conditions and sterilizing the solution.

The compound of formula I, II or III may also be administered as an infusion of a dextrose solution or a saline solution e.g., Ringers' solution.

The compounds may also be administered in other solvents such as alcohol, polyethyleneglycol and dimethylsulfoxide. They may also be administered intramuscularly as a suspension. The compounds (formulas I, II or III) of this invention may be prepared by the following methods:

METHOD 1.

Benzyltetrahydroisoquinolines are prepared in the customary fashion from appropriately substituted phenylethylamines and phenylacetic acids by the Bischler-Napieralski reaction. The tertiary benzylisoquinoline is quaternized with an appropriate α-bromo-ω-chloroalkane,α-iodo-ω-chloroalkane, or α-iodo-ω-bromoalkane. The resulting N-methyl, N-(ω-haloalkyl)-1-benzyltetrahydroisoquinolinium halide is boiled in water with the silver salt of the appropriate dicarboxylic acid, yielding silver bromide and the benzylisoquinolinium salt of the acid. This salt rearranges to the corresponding ester on heating: for example the generalized reaction is illustrated using α-bromo-ω-chloroalkane as follows:

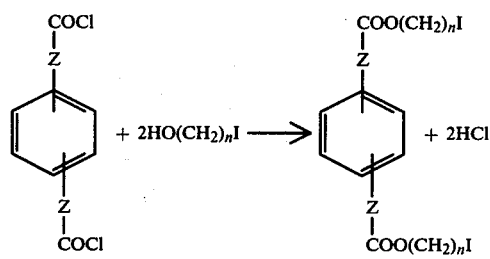

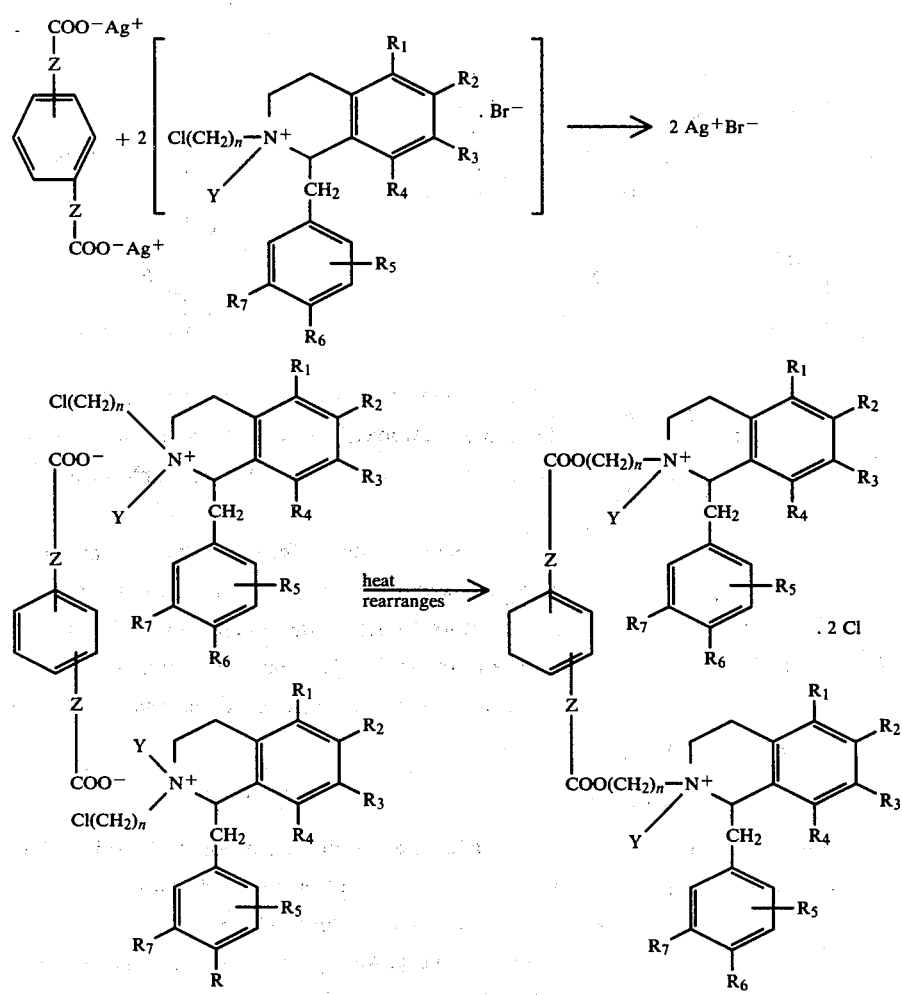

where Z is $(CH_2)_m$ and $R_1$ and $R_7$ are as defined above. Other salts are prepared by conventionally reacting the dichloro salt in an ion exchange reaction with an appropriate salt of the desired anion e.g., silver mesylate. The temperature for rearrangement is preferably 90° to 140° C.

METHOD 2.

The bis-acid chloride of an appropriate phenylene dicarboxylic acid is prepared in the usual fashion by treatment of the acid with thionyl chloride. The acid chloride is esterified with an appropriate α-hydroxy-ω-iodoalkane, yielding the desired phenylene diacyl bis-ω-iodoalkyl ester:

The diiodoester is refluxed with an excess of e.g., two moles of an appropriate 1-benzyltetrahydroisoquinoline prepared in standard fashion by the Bischler-Napieralski reaction as described in Method 1. The desired bis-benzylisoquinolinium diiodide (disalt) is obtained:

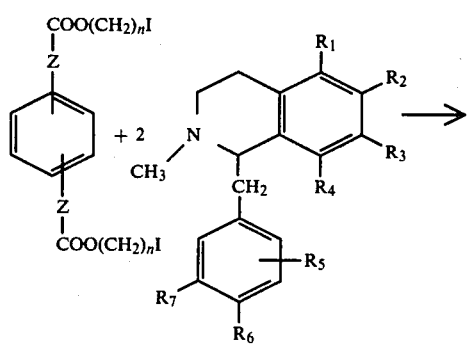

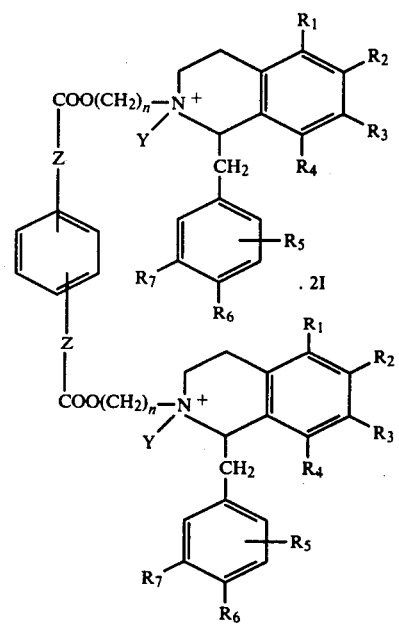

where Z is $(CH_2)_m$ and $R_1$ to $R_7$ are defined as above. The desired salts are then prepared in a conventional ion exchange reaction as described in Method 1.

Bromine or chlorine may be substituted for iodine in the α-hydroxy-ω-iodoalkane if desired and the reaction run as above.

METHOD 3

The appropriate 1-benzyltetra hydroisoquinoline prepared as described in method 1 is quaternized with the appropriate α-halogeno-ω-hydroxyalkane.

This process may be carried out in a variety of solvents (e.g., acetonitrile, lower alcohols, DMF, aromatic hydro-carbons, etc.) over temperatures ranging from ambient to reflux.

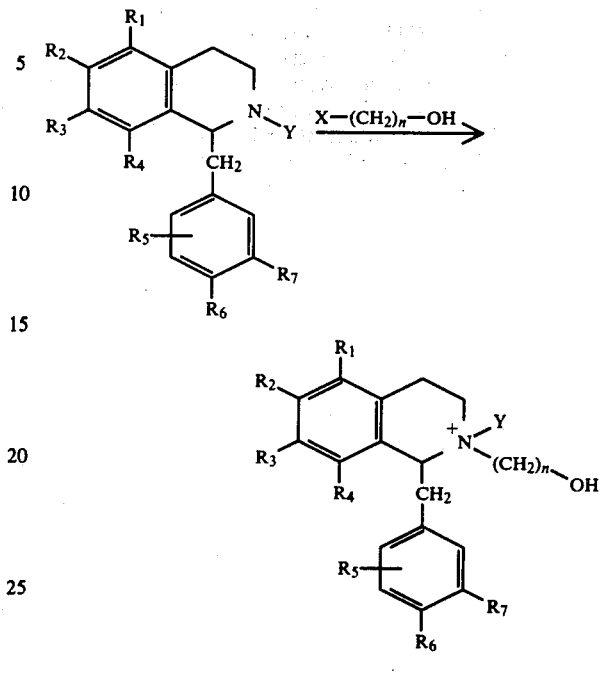

The bis acid chloride of an appropriate meta or para phenylene dicarboxylic acid is prepared in the usual fashion by treatment with a reagent such as thionyl chloride.

The bis acid chloride is then esterfied with e.g., two moles of the appropriate quaternary salt containing an ω-hydroxyalkyl chain. The desired salts are then prepared by ion exchange using conventional methods such as metathesis with a silver salt, an anion exchange resin, etc.

METHOD 4

By an alternate method, the product of the Bischler-Napieralski reaction is quaternized with 3-bromo-1-propanol in acetone at room temperature. On reduction with Zn a tetrahydroisoquinoline is obtained containing an N-(3-hydroxypropyl) substitution. This amino alcohol is acylated with the desired acid chloride in chloroform at room temperature and then refluxed for 30 minutes. Chloroform is then evaporated in vacuo, the residue is slurried in water; made alkaline by adding excess $K_2CO_3$, and extracted with ether. Ether is evaporated and the tertiary ester is dissolved in acetone. Excess methyl iodide is added and the solution is left to stand overnight. Excess ether is added to precipitate the quaternary ester. The latter is filtered and dried.

EXAMPLE (LAUDANOSINE)

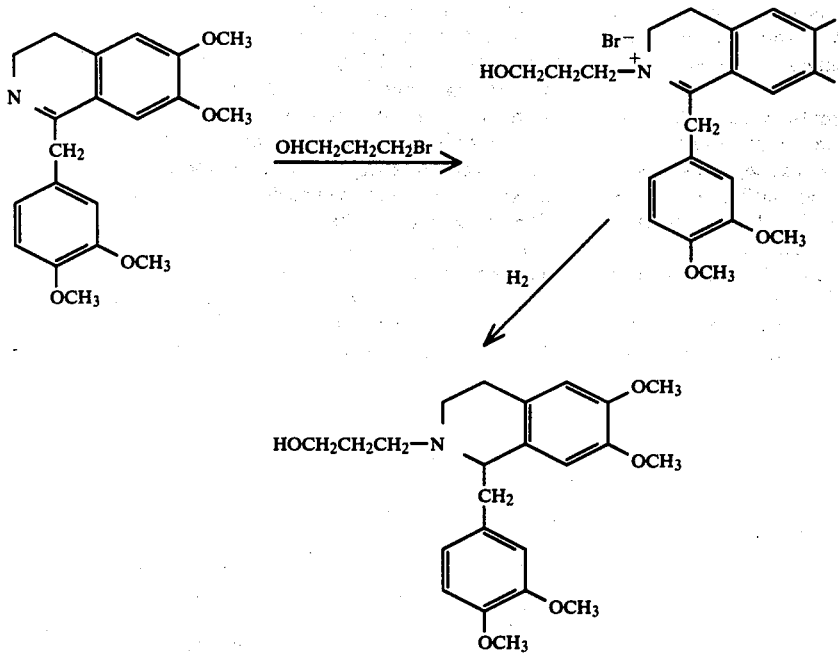

tertiary. "Amino Alcohol"
(tetrahydroisoquinoline, tertiary)

The tertiary amino alcohol is then conjugated with the appropriate acid chloride (obtained as described in Methods 2 or 3) under conditions described in Method 3 to yield the desired tertiary ester. This product may then be treated with an alkyl halide to yield the desired bis quaternary ester as set forth above. m & p-phenylene diacetic acids were commercially available (Aldrich). m and p-phenylene diacrylic acids were prepared through Knoevenagel-Doebner condensation of isophthalic and terephthalic aldehydes with malonic acid. Terephthlalic aldehyde (150 mM) and malonic acid (180 mM) were mixed with pyridine (45 ml) and piperidine (1.5 ml). The mixture was heated on a steam bath (85°-95°) for 3 hours. The solution was then cooled at room temperature and distilled in vacuum to remove pyridine. The solid residue was washed in hot isopropanol (70°) to remove residual pyridine. The product, p-phenylene diacrylic acid, was filtered and dried. (m.p. >275°).

m-phenylene diacrylic acid was prepared from isophthalaldehyde in exactly the same way. (m.p. >275°) m & p-phenylene dipropionic acids may be prepared using conventional processes by catalytic reduction e.g., by reacting the corresponding phenylene diacrylic acid with hydrogen at 40 to 45 psi gage pressure in the presence of 5% palladium on charcoal in dilute methanol or dimethyl formamide at room temperature to 55° C. For another method also see Wagner & Zook, Synthetic Organic Chemistry © 1973, see page 431 for method 26.

The compounds of this invention may sometimes include water of hydration in various amounts e.g., 1 to 5 molecules or more of water per quaternary grouping and it is intended that this invention include such compounds containing water of hydration.

The following examples illustrate the invention. Temperatures are in degrees centigrade.

EXAMPLE 1

Preparation of Bis-3-[N-methyl-1-(3,4,5-trimethoxybenzyl) 6,7-dimethoxy-1,2,3,4-tetrahydroisoquinolinium] propyl m-phenylene-3,3'-dipropionate dichloride (HH110)

1. Preparation of silver m-phenylene dipropionate

| | |
|---|---|
| m-phenylene dipropionic acid 4.4 gm = | 40 meq |
| $H_2O$ | 60 ml |
| KOH 1N | 40 ml |

The mixture is heated to boiling, and, if necessary, the pH is adjusted to 7.0 with the same acid. $AgNO_3$ 6.8 gm = 40 m M is added to the yellow hot solution. Immediately heavy precipitate forms. The mixture is cooled and filtered and the filter cake is washed with water, refiltered and dried. Yield = quantitative. The product is an amorphous, slightly colored powder. It is pulverised for use in the next step.

2. Preparation of 5'-Methoxylaudanosine

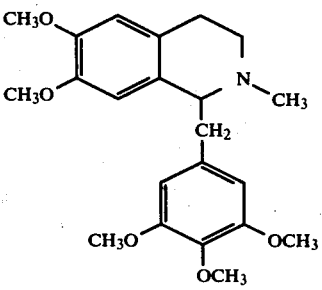

3,4-dimethoxyphenylethylamine and 3,4,5-trimethoxyphenylacetic acid are heated together at 165°–190° in a flask until bubbling of water subsides. The product N-(3,4,5-trimethoxyphenylacetyl) homoveratrylamine, is recrystallized from methanol. Yield=80%. m.p.=94°.

3.9 gm (10 mM)N-(3,4,5-trimethoxyphenylacetyl) homoveratrylamine is refluxed in 15 ml toluene together with 5 ml $POCl_3$ for 2 hours. The settled semisolids are carefully separated ($POCl_3$ excess!) and the free base liberated by adding excess of NaOH and extracted with benzene. The product, 6,7-dimethoxy-1-(3',4',5'-trimethoxybenzyl) 3,4-dihydroisoquinoline is refluxed in acetone or benzene with an excess of methyl iodide. The quaternary salt, 6,7-dimethoxy-1-(3',4',5'-trimethoxybenzyl)2-methyl 3,4-dihydroisoquinolinium io- 3. Preparation of N-(3-chloropropyl)5'-methoxylaudanosinium bromide 5'-Methoxylaudanosine 1.4 gm=4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted 5'-methoxylaudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

4. Preparation of m-phenylene dipropionic diester of N-propyl 5'-methoxylaudanosine (HH110) (Horenstein - Pahlicke Ester Formation)

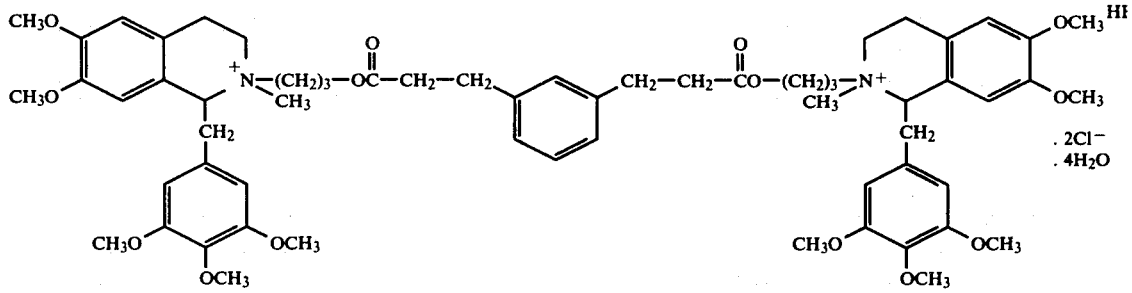

dide, precipitates out. m.p.=224°.

5.1 gm (10 mM) 6,7-dimethoxy-1-(3',4',5'-trimethoxybenzyl)2-methyl 3,4-dihydroisoquinolinium iodide is dissolved in 80 ml $H_2O$ and 16 ml concentrated HCl. Zinc dust (1.1 gm) is added in small portions to the boiling stirred solution. The yellow color disappears (reaction time 15–20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off. The ether residue does not crystallize on standing. This amine is a gummy material which hardens on standing. The crude amine is used in the next step.

| N-(3-chloropropyl)5'- | |
|---|---|
| methoxylaudanosinium bromide | 2.1 gm = 4 mM |
| Silver m-phenylene dipropionate | 0.85 gm = 4 mM |
| $H_2O$ | about 150 ml |

The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours on a steam bath (90° C.), after which rearrangement to the ester is complete:

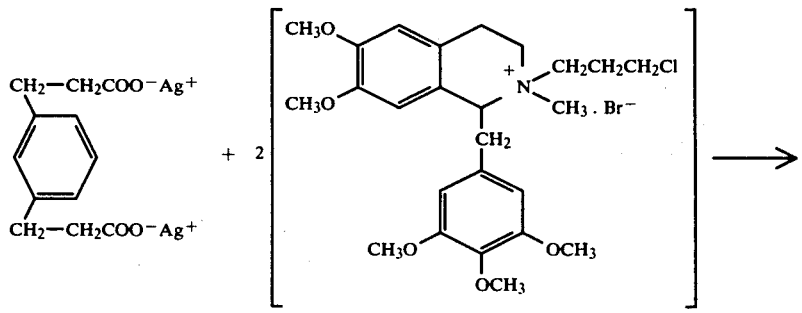

-continued

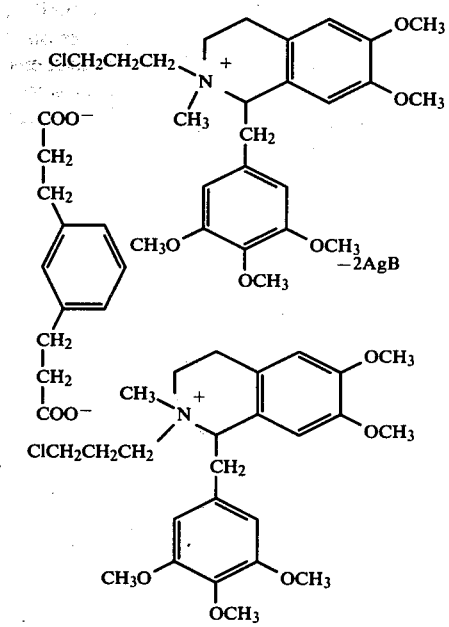

Rearranges to ester, HH-110

The amorphous residue is boiled with isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield=1.0 gm (about 40%). Yields vary from batch to batch. M.P.=80°–90° (decomposes).

| Analysis % | Calculated % | Found % |
|---|---|---|
| C | 52.99 | 53.22 |
| H | 6.46 | 5.94 |
| N | 1.99 | 2.00 |
| I | 18.06 | 19.38 | calculations assume $2H_2O$ per quaternary group.

EXAMPLE 2

Preparation of Bis-3-[N-methyl-1-(3,4,5-trimethoxybenzyl) 6,7-dimethoxy-1,2,3,4-tetrahydroisoquinolinium] propyl p-phenylene-3,3′-dipropionate dichloride (HH177)

1. Preparation of silver p-phenylene dipropionate

| | |
|---|---|
| p-phenylene dipropionic acid 4.4 gm = 40 meq, purchased from Aldrich | |
| $H_2O$ | 60 ml |
| KOH 1N | 40 ml |

The mixture is heated to boiling, and, if necessary, the pH is adjusted to 7.0 with the same acid. $AgNO_3$ 6.8 gm=40 mM is added to the yellow hot solution. Immediately a heavy precipitate forms. The mixture is cooled and filtered and the filter cake is washed with water, refiltered and dried. Yield=quantitative. The product is an amorphous, slightly colored powder. It is pulverized for use in the next step.

2. Preparation of 5′-methoxylaudanosine

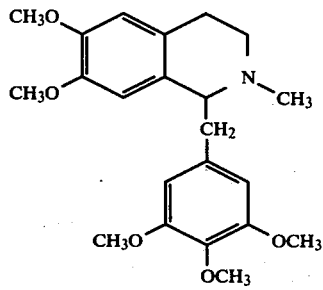

3,4-dimethoxyphenylethylamine and 3,4,5-trimethoxyphenylacetic acid are heated together at 165°–190° in a flask until bubbling of water subsides. The product, N-(3,4,5-trimethoxyphenylacetyl)homoveratrylamine, is recrystallized from methanol. Yield=80%. m.p.=94°.

3.9 gm (10 mMN-(3,4,5-trimethoxyphenylacetyl)-homoveratrylamine is refluxed in 15 ml toluene together with 5 ml $POCl_3$ for 2 hours. The settled semisolids are carefully separated ($POCl_3$ excess!) and the free base liberated by adding excess of NaOH and extracted with benzene. The product, 6,7-dimethoxy-1-(3′,4′,5′-trimethoxybenzyl) 3,4-dihydroisoquinoline is refluxed in acetone or benzene with an excess of methyl iodide. The quaternary salt, 6,7-dimethoxy-1-(3′,4′,5′-trimethoxybenzyl)2-methyl 3,4-dihydroisoquinolinium iodide, precipitates out. m.p.=224°.

5.1 gm (10 mM) 6,7-dimethoxy-1-(3′,4′,5′-trimethoxybenzyl)2-methyl 3,4-dihydroisoquinolinium iodide is dissolved in 80 ml $H_2O$ and 16 ml concentrated HCl. Zinc dust (1.1 gm) is added in small portions to the boiling stirred solution. The yellow color disappears (reaction time 15–20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off. The ether residue does not crystallize on standing. This amine is a gummy material which hardens on standing. The crude amine is used in the next step.

3. Preparation of N-(3-chloropropyl)5'-methoxylaudanosinium bromide days. (Sometimes part of the unreacted laudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield = 1.6 gm, about 80% of theory.

4. Preparation of p-phenylene dipropionic diester of N-propyl 5'methoxylaudanosine (HH177) (Horenstein - Pahlicke Ester Formation)

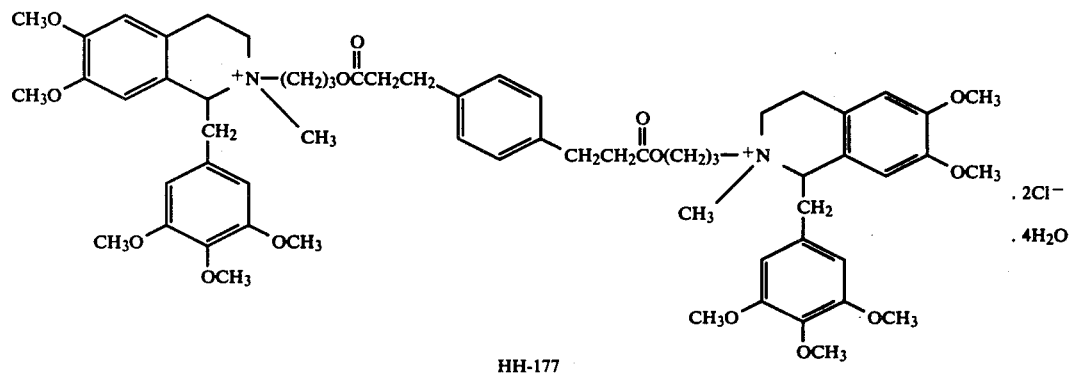

HH-177

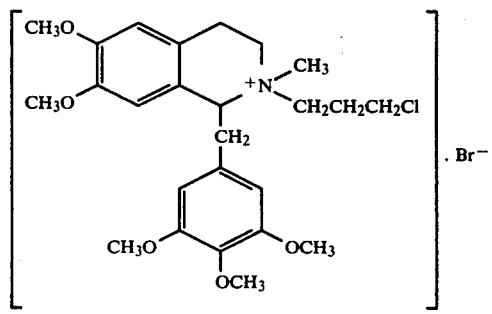

5'-Methoxylaudanosine 1.4 gm=4 mM is dissolved in 8 ml dimethylformamide by warming slightly. 1-bromo03-chloropropane 1.2 gm (about 100% excess) is added and the mixture is left at room temperature for 5

| N-(3-chloropropyl)5'-methoxylaudanosinum bromide | 2.1 gm = 4 mM |
| Silver p-phenylene dipropionate | 0.85 gm = 4 mM |
| H₂O | about 150 ml |

The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue on a steam bath (90° C.) is done for about 2 hours, after which rearrangement of the ester is complete:

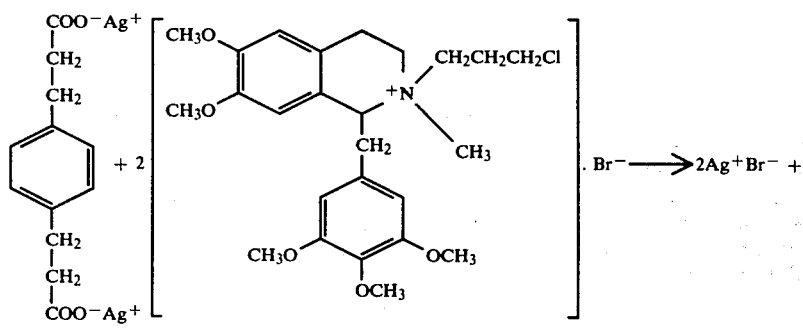

-continued

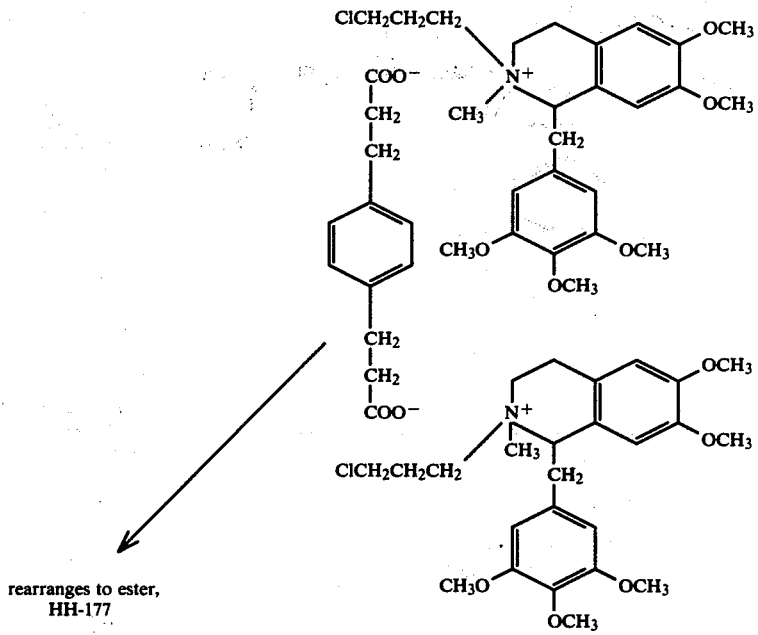

rearranges to ester, HH-177

The amorphous residue is boiled with isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield=1.0 gm (about 40%). Yields vary from batch to batch. M.P.=80–90% (decomposes).

EXAMPLE 3

Preparation of Bis-3-[N-methyl-1-(3,4-dimethoxybenzyl)6,7-dimethoxy-1,2,3,4-tetrahydroisoquinolinium] propyl p-phenylene-3,3'-dipropionate dichloride. (HH121)

1. Preparation of silver p-phenylene dipropionate

| | |
|---|---|
| p-phenylene dipropionic acid 4.4 gm = 40 meq, purchased from Aldrich | |
| H₂O | 60 ml |
| KOH 1N | 40 ml |

The mixture is heated to boiling, and, if necessary, the pH is adjusted to 7.0 with the same acid. AgNO₃ 6.8 gm=40 mM is added to the yellow hot solution. Immediately a heavy precipitate forms. The mixture is cooled and filtered and the filter cake is washed with water, refiltered and dried. Yield=quantitative. The product is an amorphous, slightly colored powder. It is pulverized for use in the next step.

2. Preparation of N-(3-chloropropyl) Laudanosinium bromide):

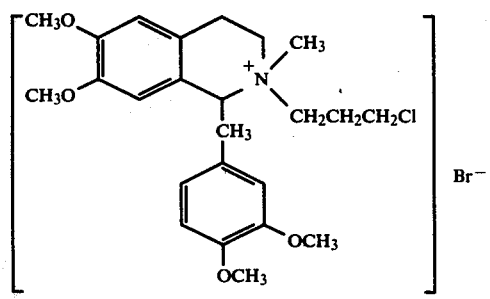

Laudanosine (Aldrich) 1.4 gm=4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted laudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

3. Preparation of p-phenylene dipropionic diester of N-propyl laudanosine (HH121)

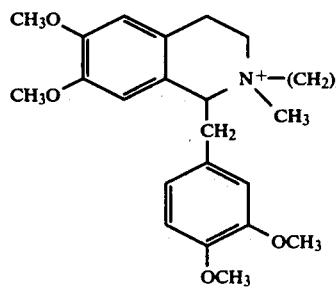
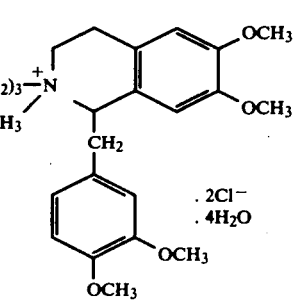

HH 121

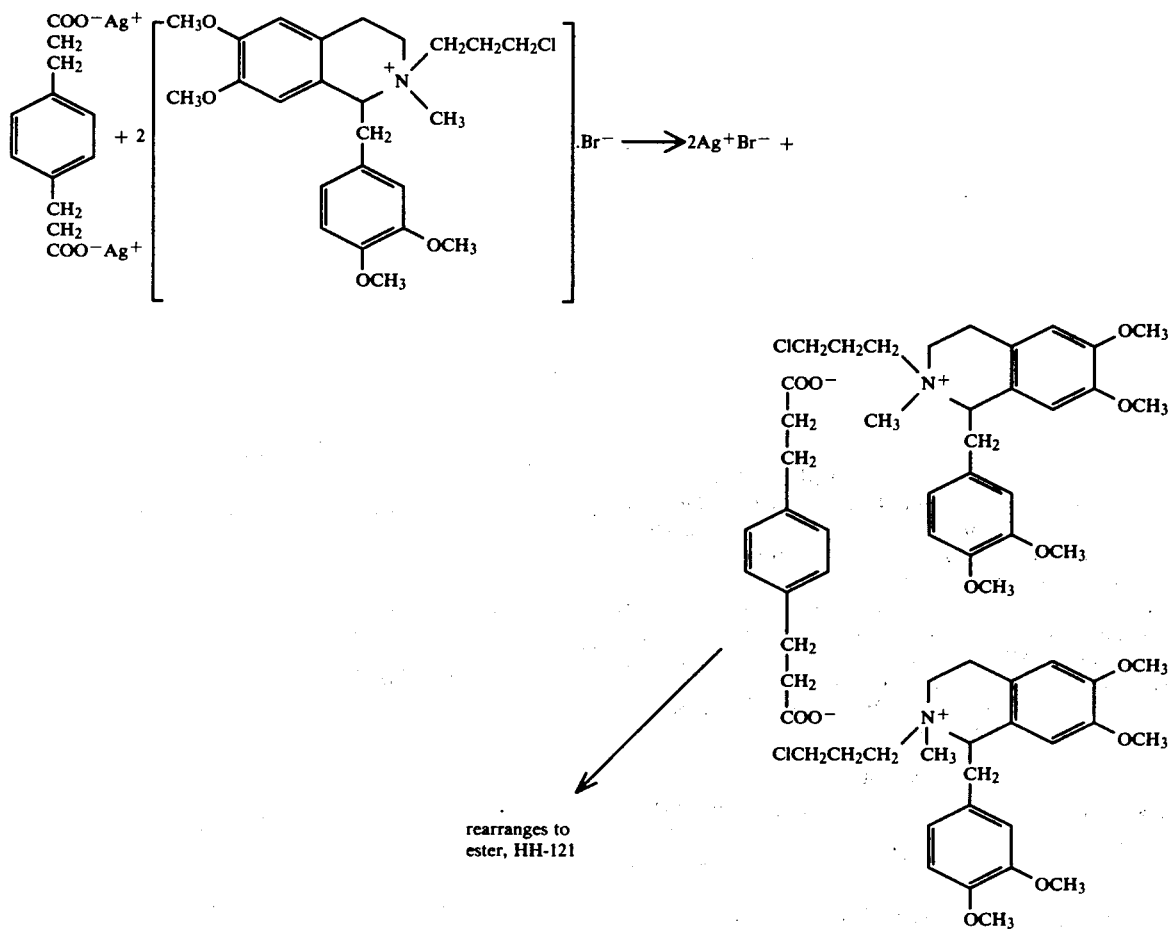

done for about 2 hours, after which the rearrangement to the ester is complete:

| | |
|---|---|
| N-(3-chloropropyl) laudanosinium bromide | 2.1 gm = 4 mM |
| Silver p-phenylene dipropionate | 0.85 gm = 4 mM |
| H₂O | about 150 ml |

The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours, after which the rearrangement to the ester is complete:

The amorphous residue is boiled to isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield = 1.0 gm (about 40%). Yields vary from batch to batch. M.P. = 80°–90° (decomposes).

| ANAYLSIS: | CALCULATED % | FOUND % |
|---|---|---|
| | C 53.57 | 53.62 |
| | H 6.44 | 6.06 |
| | N 2.08 | 2.10 |
| | I 18.87 | 18.87 |

Calculations assume 2H₂O per quaternary group.

EXAMPLE 4

Preparation of Bis-3-[N-methyl-1-(3,4-dimethoxybenzyl) 6,7-dimethoxy-1,2,3,4-tetrahydroisoquinolinium]-propyl m-phenylene-3,3'-dipropionate dichloride. (HH35)

1. Preparation of silver m-phenylene dipropionate

| m-phenylene dipropionic acid 4.4 gm = 40 meq, purchased from Aldrich | |
|---|---|
| H₂O | 60 ml |
| KOH 1N | 40 ml |

The mixture is heated to boiling, and, if necessary, the pH is adjusted to 7.0 with the same acid. AgNO₃ 6.8 gm=40 mM is added to the yellow hot solution. Immediately a heavy precipitate forms. The mixture is cooled and filtered and the filter cake is washed with water, refiltered and dried. Yield=quantitative. The product is an amorphous, slightly colored powder. It is pulverized for use in the next step.

2. Preparation of 3-chloropropyl laudanosinium bromide:

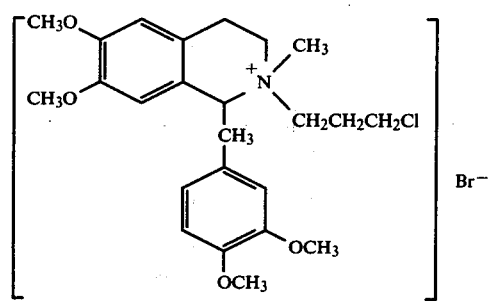

Laudanosine (Aldrich) 1.4 gm=4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted laudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

3. Preparation of m-phenylene dipropionic diester of N-propyl laudanosine (HH35).

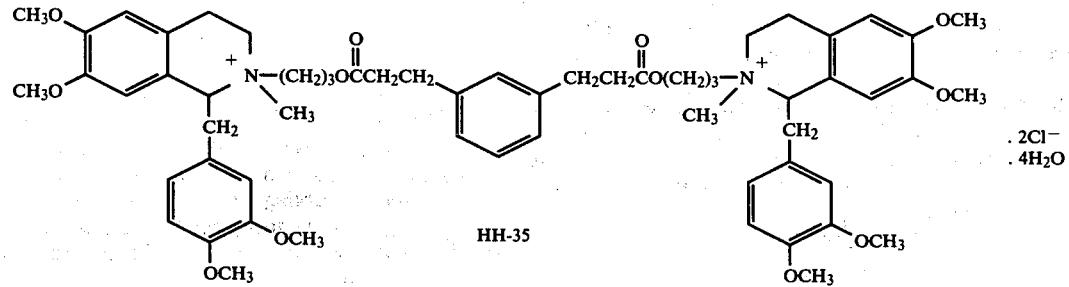

HH-35

| N-(3-chloropropyl) laudanosinium bromide | 2.1 gm = 4 mM |
|---|---|
| Silver m-phenylene dipropionate | 0.85 gm = 4 mM |
| H₂O | about 150 ml |

The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours on a steam bath at 90° C., after which the rearrangement to the ester is complete:

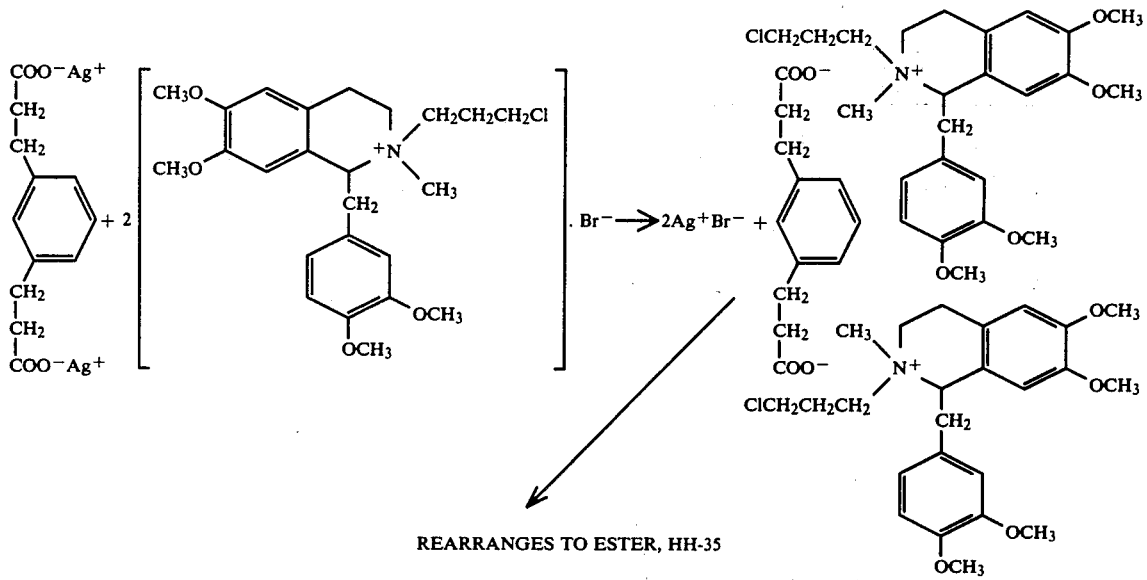

REARRANGES TO ESTER, HH-35

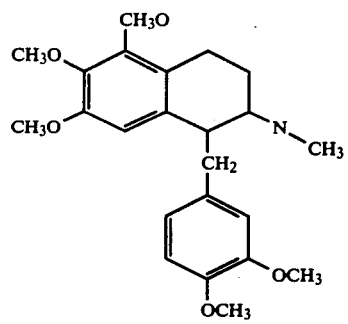

30

The amorphous residue is boiled with isopropranol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage they still probably retain water in varying degrees. Yield=1.0 gm (about 40%). Yields vary from batch to batch. M.P.=80°–90° (decomposes).

EXAMPLE 5

Preparation of Bis-3-[N-methyl-1-(3,4-dimethoxybenzyl)5,6,7-trimethoxy-1,2,3,4-tetrahydroisoquinolinium]-propyl p-phenylene-3,3'-dipropionate dichloride (LL37)

1. Preparation of silver p-phenylene dipropionate

| | |
|---|---|
| p-phenylene dipropionic acid | 4.4 gm = 40 mEq |
| H₂O | 60 ml |
| KOH 1N | 40 ml |

The mixture is heated to boiling, and, if necessary, the pH is adjusted to 7.0 with the same acid. AgNO₃ 6.8 gm=40 mM is added to the yellow hot solution. Immediately a heavy precipitate forms. The mixture is cooled and filtered and the filter cake is washed with water, refiltered and dried. Yield=quantitative. The product is an amorphous, slightly colored powder. It is pulverized for use in the next step.

2. Preparation of 5-Methoxylaudanosine [N-methyl-1-(3,4-dimethoxybenzyl)5,6,7-trimethoxy-1,2,3,4-tetrahydroisoquinoline]

2,3,4-trimethoxyphenylethylamine and 3,4-dimethoxyphenylacetic acid are heated together at 165°–190° in a flask until bubbling of water subsides. The product, N-(3,4-dimethoxyphenylacetyl)-2,3,4-trimethoxyphenylethylamine, is recrystallized from methanol. Yield=80%. m.p.=101°.

3.9 gm (10 mM) N-(3,4-dimethoxyphenylacetyl)-2,3,4-trimethoxyphenylethylamine is refluxed in 15 ml toluene together with 5 ml POCl₃ for 2 hours. The settled semisolids are carefully separated (POCl₃ excess!) and the free base liberated by adding excess of NaOH and extracted with benzene. The product, 5,6,7-trimethoxy-1-(3',4'-dimethoxybenzyl)3,4-dihydroisoquinoline, is refluxed in acetone or benzene with an excess of methyl iodide. The quaternary salt, 5,6,7-trimethoxy-1-(3',4'-dimethoxybenzyl) 2-methyl 3,4-dihydroisoquinolinium iodide, precipitates out. m.p.=165°.

5.1 gm (10 mM) 5,6,7-trimethoxy-1-(3',4'-dimethoxybenzyl)2-methyl 3,4-dihydroisoquinolinium iodide is dissolved in 80 ml H₂O and 16 ml concentrated HCl. Zinc dust (1.1 gm) is added in small portions to the boiling stirred solution. The yellow color disappears (reaction time 15–20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off.

3. Preparation of N-(3-chloropropyl)5-methoxylaudanosinium bromide 5-methoxylaudanosine 1.4 gm=4 mM is dissolved in 8 ml dimethylformamide by warming slightly. 1-bromo-3,chloropropane 1.2 gm (about 100% excess) is added and the mixture is left at room temperature for 5 days. (Sometimes part of the unreacted 5-methoxylaudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield = 1.6 gm, about 80% of theory.

4. Preparation of p-phenylene dipropionic diester of N-propyl 5-methoxylaudanosine (LL37)

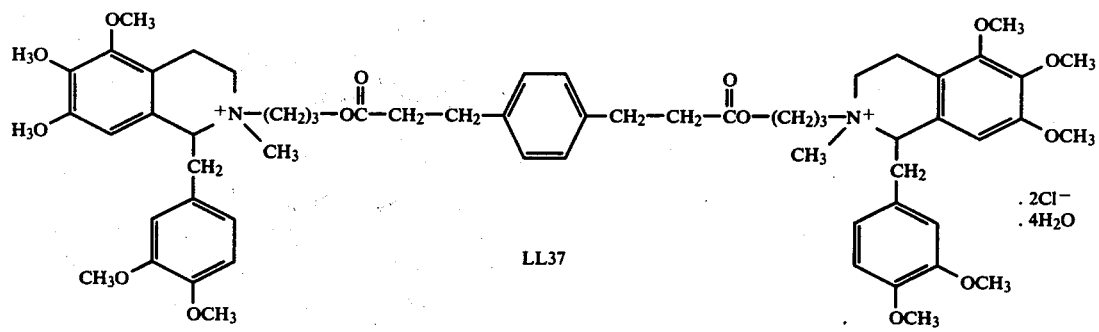

LL37

The ether residue does not crystallize on standing. This amine is a gummy material which hardens on standing. The crude amine is used in the next stop.

| | | |
|---|---|---|
| N-(3-chloropropyl)5-methoxylaudanosinium bromide | 2.1 gm | = 4 mM |
| Silver p-phenylene dipropionate | 0.85 gm | = 4 mM |
| H$_2$O | about 150 ml | |

The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours on a steam bath (90° C.), after which rearrangement to the ester is complete:

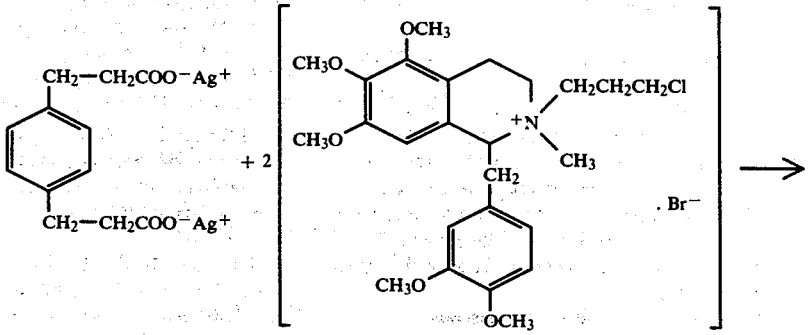

-continued

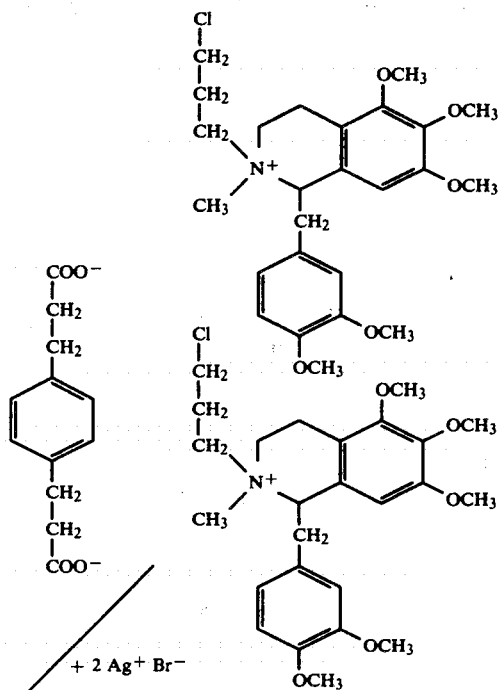

Rearranges to ester, LL37

The amorphous residue is boiled with isopropanol (about 40 ml) and filtered hot from some trace mechanical impurities. Gums precipitate from the filtrate at room temperature and the precipitation is completed at about −3° overnight. The supernatant is decanted and the material is slurried in ethyl acetate twice. By now the gum is semisolid and can be filtered off. After careful drying at 75° the gums become solids. At this stage, they still probably retain water in varying degrees. Yield = 1.0 gm (about 40%). Yields vary from batch to batch. m.p. = 80°–90° (decomposes).

EXAMPLE 6

Preparation of Bis-3-[N-methyl-1-(3,4,5-trimethoxybenzyl)5,6,7-trimethoxy-1,2,3,4-tetrahydroisoquinolinium] propyl p-phenylene-3,3'-dipropionate dichloride (KK194)

1. Preparation of silver p-phenylene dipropionate

| p-phenylene dipropionic acid | 4.4 gm = 40 mEq |
|---|---|
| H₂O | 60 ml |
| KOH 1N | 40 ml |

The mixture is heated to boiling, and, if necessary, the pH is adjusted to 7.0 with the same acid. AgNO₃ 6.8 gm = 40 mM is added to the hot solution. Immediately a heavy precipitate forms. The mixture is cooled and filtered, and the filter cake is washed with water, refiltered and dried. Yield = quantitative. The product is an amorphous, slightly colored powder. It is pulverized for use in the next step.

2. Preparation of 5,5'-dimethoxylaudanosine

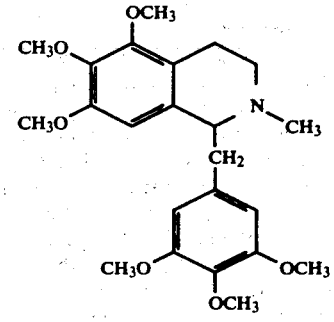

2,3,4-dimethoxyphenylethylamine and 3,4,5-trimethoxyphenylacetic acid are heated together at 165°–190° in a flask until bubbling of water subsides. The product, N-(3,4,5-trimethoxyphenylacetyl)-2,3,4-trimethoxyphenylethylamine, is recrystallized from methanol. Yield = 80%. m.p. = 85°.

3.9 gm (10 mM) N-(3,4,5-trimethoxyphenylacetyl)-2,3,4-trimethoxyphenylethylamine is refluxed in 15 ml toluene together with 5 ml POCl₃ for two hours. The settled semisolids are carefully separated (POCl₃ excess→) and the free base liberated by adding excess of NaOH and extracted with benzene. The product, 5,6,7-trimethoxy-1-(3',4',5'-trimethoxybenzyl)-3,4-dihydroisoquinoline, is refluxed in acetone or benzene with an excess of methyl iodide. The quaternary salt, 5,6,7-trimethoxy-1-(3',4',5'-trimethoxybenzyl)-2-methyl-3,4-dihydroisoquinolinium iodide, precipitates out. m.p. = 181°.

5.1 gm (10 mM) 5,6,7-trimethoxy-1-(3',4',5'-trimethoxybenzyl)-2-methyl-3,4-dihydroisoquinolinium iodide is dissolved in 80 ml H₂O and 16 ml concentrated HCl. Zinc dust (1.1 gm) is added in small portions to the boiling stirred solution. The yellow color disappears (reaction time 15–20 minutes). The mixture is filtered hot from some unreacted zinc and rendered alkaline with concentrated NaOH. It is impractical to filter the partly precipitated zinc hydroxide, so to avoid emulsions, the whole mixture is carefully shaken with chloroform. The residue of the chloroform solution is redissolved in ether and the ether insolubles are filtered off. The ether residue does not crystallize on standing. This amine is a gummy material which hardens on standing. The crude amine is used in the next step.

3. Preparation of N-(3-chloropropyl)5,5'-dimethoxylaudanosinium bromide 5,5'-dimethoxylaudanosine 1.4 gm=4 mM is dissolved in 8 ml dimethylformamide by warming slightly. 1-bromo-3-chloropropane 1.2 gm (about 100% excess) is added and the mixture is left at room temperature for 5 days. (Sometimes part of the unreacted 5,5'-dimethoxylaudanosine crystallizes out, but eventually it redissolves).

The reddish-orange solution is treated with a large amount of ether and the precipitated gummy quaternary salt is decanted and slurried in fresh ether. After standing in ether for one day, low melting solids are obtained. Yield=1.6 gm, about 80% of theory.

4. Preparation of p-phenylene dipropionic diester of N-propyl 5'-methoxylaudanosine (KK194)

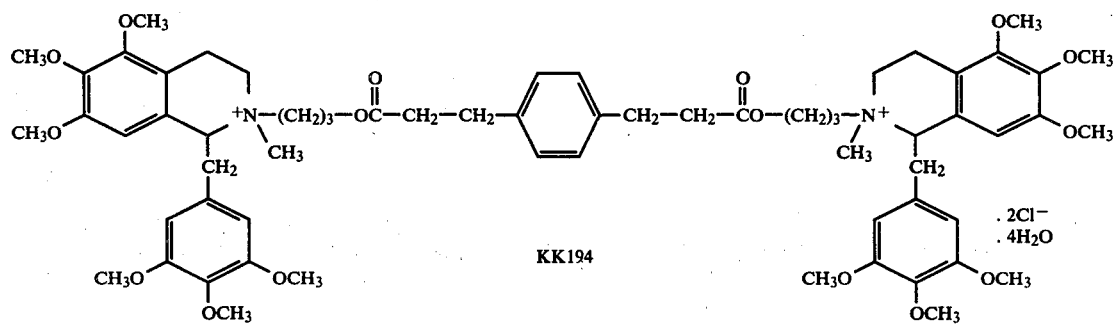

KK194

| | |
|---|---|
| N-(3-chloropropyl)-5,5'-dimethoxylaudanosinium bromide | 2.1 gm = 4 mM |
| Silver p-phenylene dipropionate | 0.85 gm = 4 mM |
| H$_2$O | about 150 ml |

The mixture is boiled in an open beaker for about 10–15 minutes, stirring by hand from time to time. At the boiling temperature the silver salt is slightly soluble and reacts with the quaternary bromide. The mixture is cooled to room temperature, filtered straight and the aqueous solution is evaporated to dryness in a large dish on a steam bath. Continued heating of the residue is done for about 2 hours on a steam bath (90° C.), after which rearrangement to the ester is complete:

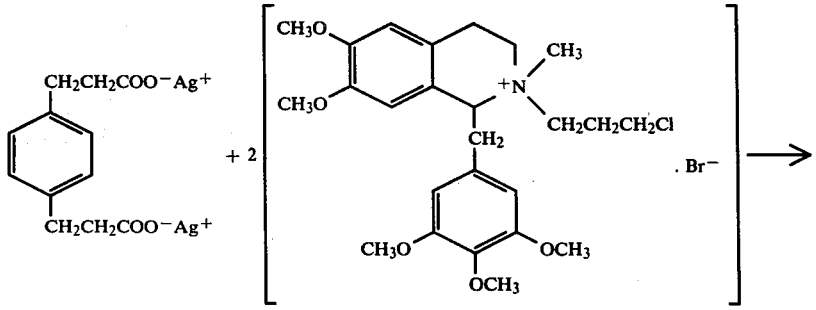

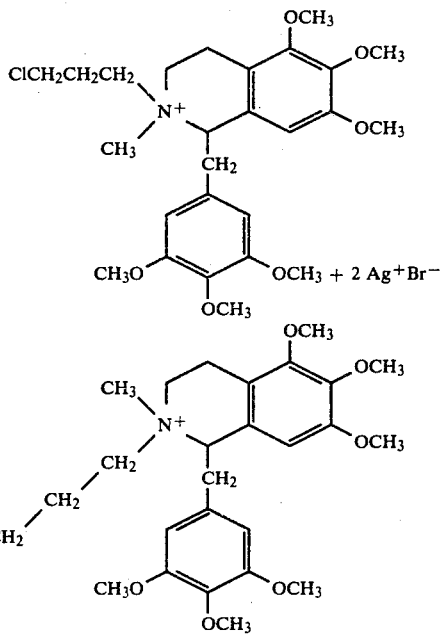

Rearranges to ester, KK194

EXAMPLE 7

Pharmaceutical formulation (HH 110) is dissolved in water for injection to a concentration of 10 mg/ml. The solution is then poured into 20 ml vials which are then sealed.

EXAMPLE 8

Sterile (HH 110) powder (100 mg) is aseptically packaged in 20 ml vials sealed with a rubber-stopper. Ten ml sterile water for injection is added to the vials in order to produce a 1 percent (10 mg/ml) solution of (HH 110).

EXAMPLE 9

The compounds HH 110, HH 177, HH 121, and HH 35 were each separately dissolved in 0.9 percent saline at a concentration of 2 mg/ml. Cynomolgus monkeys are anesthetized iwth halothane, nitrous oxide and oxygen. The maintenance concentration of halothane was 1.0%. Arterial and venous catheters were placed in the femoral vessels for drug administration and recording of the arterial pressure. Controlled ventilation was accomplished via an endotrachael tube. Twitch and tetanic contractions of the tibialis arterior muscle were elicited indirectly via the sciatic nerve. Recordings of arterial pressure electrocardiogram (lead I), heart rate, and muscle function were made simultaneously.

EXAMPLE 10

Bis-3-[N-methyl-1-(3,4,5-trimethoxy benzyl)-6, 7-dimethoxy-1,2,3,4-tetrahydroisoquinolinium]propyl m-phenylene-3,3'-dipropionate dimesylate is prepared in an ion exchange reaction by reacting HH110 with silver mesylate. The dichloride HH110 is dissolved in acetonitrile as is the silver mesylate. The reaction mixture is stirred at room temperature for 30 minutes to form the silver chloride precipitate. The mixture is filtered through filter paper to remove the silver chloride thereby leaving the mesylate salt in solution. The acetonitrile is then evaporated.

The product is then dissolved in ethanol and filtered to remove residual silver mesylate. The ethanol is then evaporated.

EXAMPLE 11

Preparation of bis-3-[N-Methyl-1-(3,4,5-trimethoxybenzyl)-6,7-dimethoxy-1,2,3,4-tetrahydroisoquinolinium]-propyl m-phenylene-3,3'-dipropionate diiodide tetrahydrate N-(3-hydroxypropyl)-5'-methoxylaudanosinium iodide, 3.2 g, was dissolved in dry acetonitrile and 4 g of molecular sieve #4 was added. After stirring for 24 hours at room temperature m-phenylene dipropionyl dichloride [prepared by action of thionyl chloride on the known m-phenylene dipropionic acid; F. S. Kipping, J. Chem. Soc., 53, 21 (1888)], 0.78 g, was added followed by another 4 g of molecular sieve #4. The mixture was stirred for 24–48 hours at room temperature, filtered and evaporated to dryness giving a dark brown oil which was dissolved in hot ethanol and reprecipitated as a light brown oil by cooling. The oil solidified to a light brown amorphous solid after drying. A 60% yield was obtained.

This procedure was also used to prepare related compounds by substituting para-phenylene dipropionyl dichloride for the meta isomer and N-(3-hydroxypropy laudanosinium iodide for the 5'-methoxylaudanosinium iodide.

EXAMPLE 12

Preparation of N-(3-hydroxypropyl)-5'-methoxylaudanosinium iodide

One gram of 5'-methoxylaudanosine [J. Russell Flack, L. L. Miller and F. R. Stermitz - Tetrahedron, 30, 931 (1974)] in 20 ml. of dry acetonitrile was refluxed with 1.2 g of 1-iodo-3-propanol [S. Wawzonek, J. Org.

Chem., 25, 2068 (1960)] for 24 hours. The mixture was filtered; solvent was evaporated under vacuum and ether was added to precipitate a yellow oily solid. After decanting the ether and drying at 60° a yellow powder was obtained in quantitative yield.

The same procedure was used to prepare N-(3-hydroxypropyl) laudanosinium iodide.

EXAMPLE 13

1,2,3,4-Tetrahydroisoquinolines

These compounds were prepared by cyclodehydration of β-phenylethylamides to 3,4-dihydroisoquinolines which were quaternized with $CH_3$ and then reduced by Zn in hot HCl to the corresponding 1,2,3,4-tetrahydroisoquinolines.

For example, laudanosine [1-(3,4-dimethoxybenzyl)-2-methyl-1,2,3,4-tetrahydroisoquinoline] was prepared in the following manner: 3,4-dimethoxyphenylethylamine (Aldrich) (100 mM) was mixed with 3,4-dimethoxyphenylacetic acid (Aldrich) (100 mM) and heated at 190°–200° until bubbling stops (20 minutes). The product (homoveratroylhomoveratrylamine) is cooled and recrystallized from methanol. Yield=85%. m.p.=122°. Homoveratroylhomoveratrylamine (100 mM) was mixed with 250 ml toluene and 50 ml $POCl_3$ and heated to boiling for 2 hours, then cooled to room temperature. The crystalloid precipitate was filtered, rinsed with petroleum ether, dissolved in water, rendered alkaline with excess of $NH_3$ and extracted with benzene. The solution was then dried with sodium sulfate, filtered, and excess methyl iodide was added. The solution was refluxed for 15 minutes, and then left to stand at room temperature for twelve hours. The quaternary salt, dihydropapaverine methiodide, precipitates out. 100 mM of this quaternary salt is then reduced by boiling with 12 gm zinc dust in 600 ml water and 120 ml concentrated hydrochloric acid for one hour, and filtered hot to remove unreacted zinc. Excess ammonia is then added and the product is extracted with chloroform. The chloroform is then evaporated and the product (laudanosine) is extracted with petroleum ether, from which it crystallizes on cooling. m.p.=114°–115°. By an analogous procedure to that described above for the synthesis of laudanosine, the corresponding benzylisoquinoline may be prepared from the analogous starting materials. For example:

- 3,4-dimethoxyphenylethylamine and 3,4,5-trimethoxyphenylacetic acid (to yield 5'-methoxylaudanosine);
- 2,3,4-trimethoxyphenylethylamine and 3,4-dimethoxyphenylacetic acid (to yield 5-methoxylaudanosine;
- 3,4,5-trimethoxyphenylethylamine (mescaline) and 3,4-dimethoxyphenylacetic acid (to yield 8-methoxylaudanosine);
- 2,3,4-trimethoxyphenylethylamine and 3,4,5-trimethoxyphenylacetic acid (to yield 5,5'-dimethoxylaudanosine);
- 3,4,5-trimethoxyphenylethylamine and 3,4,5-trimethoxyphenylacetic acid (to yield 8,5'-dimethoxylaudanosine).

The above compounds are then reacted as in Methods 1 to 4 to prepare the compounds of this invention.

As shown in Table 1, four to six animals received each compound. Four additional animals received succinylcholine chloride or d-tubocurarine chloride as controls. The chart shows the dose range required to produce 95 percent block of the twitch response of the tibiolis anterior muscle under above anesthetic conditions in each series of animals receiving each drug. Also listed in the chart is the range of the duration of action of each compound in each series of animals. Duration of action is defined as the time span from drug injection to full recovery of the twitch response of the tibialis anterior muscle.

The duration of action of these compounds in monkeys is more indicative of the possible duration of action of the compounds in man than studies done in other species, such as the cat and dog, for the following reason: the compounds are believed to be broken down (hydrolyzed) by an enzyme (plasma cholinesterase) present in man, monkey, cat and dog. The rate of breakdown of any compound by this enzyme is believed to be the principal determinant of its duration of action in the body. The plasma cholinesterase activity of the monkey is known to be most similar to that of man (c.f. Hobbiger and Peck, British Journal of Pharmacology 37: 258–271, 1969).

TABLE 1

Neuromuscular Blocking Potency of Selected Compounds In The Cynomolgus Monkey

| Compound | Number of Animals Tested | $ED_{95}$* (MG/RG Cation) | Range Of Duration Of Action (Minute From Injection to Full Recovery) |
|---|---|---|---|
| HH 110 | 6 | 0.5–1.0 | 5–8 |
| HH 177 | 4 | 0.5–1.0 | 8–12 |
| HH 121 | 6 | 2.0–4.0 | 4–6 |
| HH 35 | 4 | 2.0–4.0 | 3–5 |
| Succinylcholine | 4 | 1.0–2.0 | 4–6 |
| d-Tubocurarine | 4 | 0.2–0.4 | 30–50 |

*$ED_{95}$ means the dose necessary to produce 95 percent block of the twitch response of the tibialis anterior muscle stimulated indirectly at 0.15 HZ via the sciatic nerve.

We claim:
1. A compound of the formula (I)

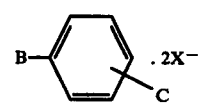

where B and C are each

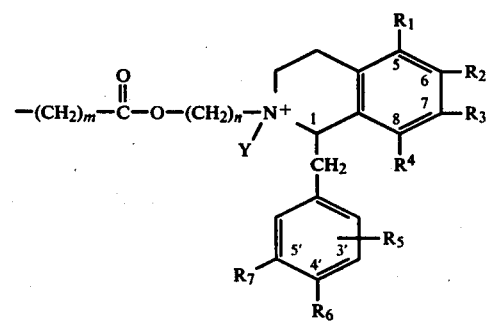

where
m is 2, 3 or 4,
C is para or meta to B,
n is 2, 3 or 4

$R_1$, $R_2$, $R_3$, $R_4$, $R_5$, $R_6$ and $R_7$ are the same or different and are each hydrogen or lower alkoxy of 1 to 4 carbon atoms, Y is lower alkyl of 1 to 4 carbon atoms, and X is a pharmaceutically acceptable anion, provided that at least one of $R_1$ and $R_4$ is lower alkoxy and at least one of $R_5$ and $R_7$ is lower alkoxy.

2. The compound of claim 1 where m=2, n=3, Y is methyl, one or two of $R_1$ and $R_4$ are hydrogen and the others are methoxy and two or three of $R_5$ and $R_7$ are methoxy and when two are methoxy the other is hydrogen.

3. The compound of claim 1 where m=2 n=3, Y is methyl, $R_1$ and $R_4$ are hydrogen, $R_2$ and $R_3$ are methoxy, $R_5$ and $R_6$ and $R_7$ are methoxy at the 3, 4 and 5 position of the phenyl ring.

4. The compound of claim 3 where C is para to B.

5. The compound of claim 3 where C is meta to B.

6. The compound of claim 1 where m=2, n=3, Y is methyl, $R_1$ and $R_4$ are hydrogen, $R_2$ and $R_3$ are methoxy, $R_5$ and $R_6$ are methoxy and $R_7$ is hydrogen.

7. The compound of claim 6 where C is para to B.

8. The compound of claim 1 in which X is mesylate or chloride.

9. The compound of claim 4 in which X is mesylate, or chloride.

10. The compound of claim 5 in which X is mesylate, or chloride.

11. The compound of claim 7 in which X is mesylate, or chloride.

12. The method of producing muscle relaxation in a mammal which comprises parenterally administering to said mammal an effective neuromuscular blocking amount of a compound of the formula (I)

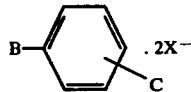
(I)

where B and C are each

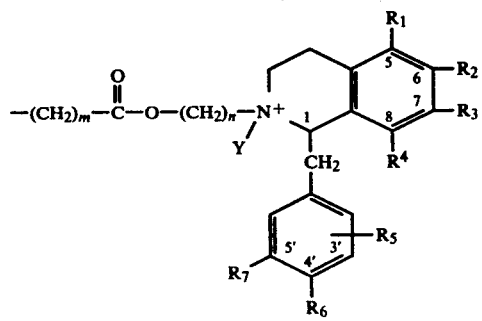

where m is 2, 3 or 4,

C is para or meta to B, $R_1$, $R_2$, $R_3$, $R_4$, $R_5$, $R_6$ and $R_7$ are the same or different and are each hydrogen or lower alkoxy of 1 to 4 carbon atoms, Y is lower alkyl of 1 to 4 carbon atoms, and X is a pharmaceutically acceptable anion, provided that at least one of $R_1$ to $R_4$ is lower alkoxy and at least one of $R_5$ to $R_7$ is lower alkoxy.

13. Method of claim 12 where m=2, n=3, Y is methyl, one or two of $R_1$ to $R_4$ are hydrogen and the others are methoxy and two or three of $R_5$ and $R_7$ are methoxy and when two are methoxy the other is hydrogen.

14. The method of claim 12 where m=2, n=3, Y is methyl, $R_1$ and $R_4$ are hydrogen, $R_2$ and $R_3$ are methoxy, $R_5$ and $R_6$ and $R_7$ are methoxy at the 3, 4, and 5 position of the phenyl ring.

15. The method of claim 14 where C is para to B.

16. The method of claim 14 where C is meta to B.

17. The method of claim 12 where m=2, n=3, Y is methyl, $R_1$ and $R_4$ are hydrogen, $R_2$ and $R_3$ are methoxy, $R_5$ and $R_6$ are methoxy and $R_7$ is hydrogen.

18. The method of claim 17 where C is para to B.

19. The method of claim 12 in which X is mesylate, or chloride.

20. The method of claim 15 in which X is mesylate, or chloride.

21. The method of claim 16 in which X is mesylate, or chloride.

22. The method of claim 18 in which X is iodide, mesylate, tosylate, bromide, chloride, sulfate, phosphate, hydrogen phosphate, acetate or propionate.

23. The method of claim 17 in which X is iodide, mesylate, tosylate, bromide, chloride, sulfate, phosphate, hydrogen phosphate, acetate or propionate.

24. The method of claim 12 in which the compound is intravenously or intramuscularly administered.

25. The method of claim 15 in which the compound is intravenously or intramuscularly administered.

26. The method of claim 16 in which the compound is intravenously or intramuscularly administered.

27. The method of claim 24 in which the mammal is a human.

28. The method of claim 25 in which the mammal is a human.

29. The method of claim 26 in which the mammal is a human.

30. Bis-3-[N-methyl-1-(3,4,5-trimethoxy benzyl)6,7-dimethoxy-1,2,3,4-tetrahydroisoquinolinium]propyl m-phenylene-3,3'-dipropionate dichloride.

31. Bis-3-[N-methyl-1-(3,4,5-trimethoxy benzyl)6,7-dimethoxy-1,2,3,4-tetrahydroisoquinolinium]propyl m-phenylene-3,3'-dipropionate dimesylate.

32. A pharmaceutical preparation for the parenteral administration comprising an effective neuromuscular blocking amount of the compound of the formula (I)

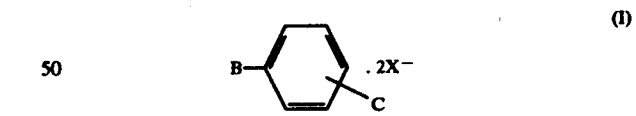
(I)

where B and C are each

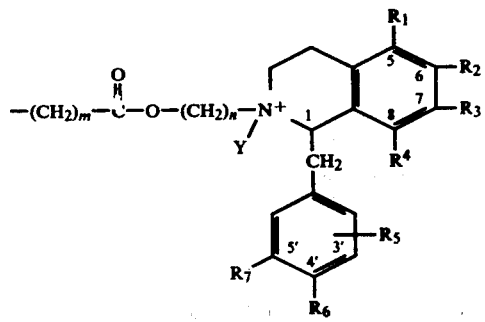

where
- m is, 2, 3 or 4,
- C is para or meta to B,
- n is 2, 3 or 4,
- $R_1$, $R_2$, $R_3$, $R_4$, $R_5$, $R_6$ and $R_7$ are the same or different and are each hydrogen or lower alkoxyl of 1 to 4 carbon atoms, Y is lower alkyl of 1 to 4 carbon atoms,
- X is a pharmaceutically acceptable anion, provided that at least one or $R_1$ to $R_4$ is lower alkoxyl and at least one of $R_5$ to $R_7$ is lower alkoxyl, and a pharmaceutically acceptable liquid carrier therefore.

33. The preparation of claim 32, wherein m=2, n=3, Y is methyl, one or two of $R_1$ to $R_4$ are hydrogen and the others are methoxy and two or three of $R_5$ to $R_6$ are methoxy and when two are methoxy the other is hydrogen.

34. The preparation of claim 32 where m=2, n=3, Y is methyl, $R_1$ and $R_4$ are hydrogen, $R_2$ and $R_3$ are methoxy, $R_5$ and $R_6$ and $R_7$ are methoxy at the 3, 4 and 5 position of the phenyl ring.

35. The preparation of claim 34 where C is para to B.

36. The preparation of claim 34 where C is meta to B.

37. The preparation of claim 32 where m=2, n=3, Y is methyl, $R_1$ and $R_4$ are hydrogen, $R_2$ and $R_3$ are methoxy, $R_5$ and $R_6$ are methoxy and $R_7$ is hydrogen.

38. The preparation of claim 37 where C is para to B.

39. The preparation of claim 32 in which X is mesylate, or chloride.

40. The preparation of claim 35 in which X is mesylate, or chloride.

41. The preparation of claim 36 in which X is mesylate, or chloride.

42. The preparation of claim 35 in which the anion is chloride or mesylate.

43. The preparation of claim 36 in which the anion is chloride or mesylate.

44. The compound of claim 1 in which the cation is Bis-3-[N-methyl-1-(3,4,-dimethoxybenzyl)-5,6,7-trimethoxy-1,2,3,4-tetrahydroisoquinolinium] propyl p-phenylene-3,3'-dipropionate.

45. The compound of claim 1 in which the cation is Bis-3-[N-methyl-1-(3,4,5-trimethoxybenzyl)-5,6,7-trimethoxy-1,2,3,4-tetrahydroisoquinolinium] propyl p-phenylene-3,3'-dipropionate.

46. Bis-3-[N-methyl-1-(3,4,5-trimethoxybenzyl)-6,7-dimethoxy-1,2,3,4-tetrahydroisoquinolinium]propyl m-phenylene-3,3'-dipropionate dichloride.

47. The method of producing muscle relaxation in a mammal which comprises parenterally administering to said mammal an effective neuromuscular blocking amount of the compound Bis-3-[N-methyl-1-(3,4,5-trimethoxybenzyl)-6,7-dimethoxy-1,2,3,4-tetrahydroisoquinolinium]propyl m-phenylene-3,3'-dipropionate dichloride.

48. The method of claim 47 in which the compound is administered in a pharmaceutically acceptable carrier therefore.

49. The method of claim 47 in which the compound is administered intravenously or intramuscularly.

50. A pharmaceutical preparation for parenteral administration for use as a muscle relaxant comprising the compound Bis-3-[N-methyl-1-(3,4,5-trimethoxybenzyl)-6,7-dimethoxy-1,2,3,4-tetrahydroisoquinolinium]propyl m-phenylene-3,3'-dipropionate dichloride and a pharmaceutically acceptable carrier therefore.

51. The preparation of claim 50 in unit dose form and comprising an effective neuromuscular blocking amount of the compound.

52. A sealed vial containing the compound of Bis-3-[N-methyl-1-(3,4,5-trimethoxybenzyl)-6,7-dimethoxy-1,2,3,4-tetrahydroisoquinolinium]propyl m-phenylene-3,3'-dipropionate dichloride as a powder.

53. The method of producing muscle relaxation in a mammal which comprises parenterally administering to said mammal an effective neuromuscular blocking amount of the compound Bis-3-[N-methyl-1-(3,4,5-trimethoxybenzyl)-1,2,3,4-tetrahydroisoquinolinium]-propyl p-phenylene-3,3'-dipropionate dichloride.

54. A pharmaceutical preparation for parenterial administration for use as a muscle relaxant comprising the compound Bis-3-[N-methyl-1-(3,4,5-trimethoxybenzyl)-1,2,3,4-tetrahydroisoquinolinium]-propyl p-phenylene-3,3'-dipropionate dichloride.

* * * * *